United States Patent [19]

Dressler et al.

[11] Patent Number: 4,592,783
[45] Date of Patent: Jun. 3, 1986

[54] RUST PREVENTIVES

[75] Inventors: Hans Dressler, Monroeville; Samuel N. Holter, Pittsburgh; Nancy Znidarsic, North Braddock, all of Pa.

[73] Assignee: Koppers Company, Inc., Pittsburgh, Pa.

[21] Appl. No.: 663,213

[22] Filed: Oct. 22, 1984

[51] Int. Cl.$^4$ ............................................. C04B 9/02
[52] U.S. Cl. ........................... 106/14.05; 106/14.29; 106/14.38; 260/505 C; 556/119
[58] Field of Search ................ 260/505 C, 429.9; 106/14.05, 14.29, 14.38, 14.43

[56] References Cited

U.S. PATENT DOCUMENTS

| | | | |
|---|---|---|---|
| 2,463,497 | 3/1949 | Smith et al. | 260/505 C |
| 2,679,482 | 5/1954 | Ross | 252/539 |
| 4,145,302 | 3/1979 | Doan | 252/539 |

OTHER PUBLICATIONS

Garbutt et al., *J. Chem. Soc.*, 1965, p. 2324.
Belov et al., Chem-Tech Fuels and Oils, 20 (3 & 4), Mar.-Apr., 1984.

*Primary Examiner*—Lorenzo B. Hayes
*Attorney, Agent, or Firm*—Donald M. MacKay; Herbert J. Zeh, Jr.

[57] ABSTRACT

Rust preventives are provided comprising divalent metal salts of the formula:

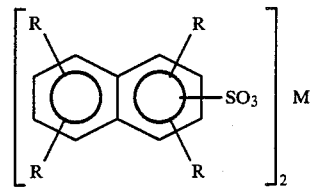

wherein the R groups are independently selected from methyl, hydrogen, and decyl of the formula:

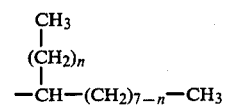

wherein n=0 to 3; and wherein from two to three R groups are decyl, zero to two R groups are methyl, and zero to two R groups are hydrogen; and M is a divalent metal selected from Mg, Ca, Ba, and Zn. Useful intermediates for preparing the said rust preventives are also provided.

16 Claims, No Drawings

RUST PREVENTIVES

BRIEF DESCRIPTION OF THE INVENTION

This invention relates to rust preventives comprising divalent metal salts of the formula:

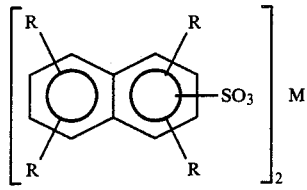

wherein the R groups are independently selected from methyl, hydrogen, and decyl of the formula:

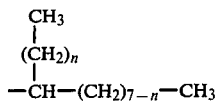

wherein n=0 to 3; and wherein from two to three R groups are decyl, zero to two R groups are methyl, and zero to two R groups are hydrogen; and M is a divalent metal selected from Mg, Ca, Ba, and Zn. These compositions can be readily overbased, if desired.

DETAILED DESCRIPTION OF THE INVENTION

The salts of the invention are prepared by first alkylating napthalene or a methyl-or dimethyl-naphthalene (hereinafter for convenience referred to as naphthalene) with an alpha olefin (preferably 1-decene) or an isomeric mixture of decenes in the presence of a catalyst. Preferred catalysts are alumino silicate catalysts, particularly activated clays such as Filtrol 13LM, 20, 24 and XJ8303 manufactured by Filtrol Corporation. Other catalysts can be employed, such as zeolites.

The molar ratio of naphthalene to olefin (hereinafter intended to include mixtures of olefins) should be about 1:2 and the amount of catalyst may vary, but should be preferably about 10–20% by weight based on the naphthalene.

The mixture, preferably blanketed with nitrogen, is heated at elevated temperatures at between about 160° C. and about 300° C. for a time between about 15 minutes and about 6 hours under autogenous pressure.

In order to inhibit olefin oligomerization, it has been found advantageous to limit the amount of olefin in the original charge and to incrementally add all or part of the olefin at reaction temperature. Typically, the initial charge contains from between 0 and about 25% of the total olefin. The balance of the olefin is added over a period of ½ to 3 hours, preferably 1 to 2 hours.

After the reaction is substantially complete, the catalyst is removed by filtration. Monoalkyl-substituted naphthalene, any unreacted materials, and any by-products are removed by distillation under reduced pressure of between about 0.1 and about 15 torr at a vapor temperature of between about 20° C. and about 240° C. until the product in the reactor is predominantly alkylated naphthalene of the formula:

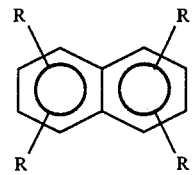

wherein the R groups are independently selected from methyl, hydrogen, and decyl of the formula

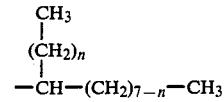

wherein n=0 to 3; and wherein from two to three R groups are decyl, zero to two R groups are methyl, and zero to two R groups are hydrogen. The monodecylnaphthalene content should be kept to a minimum, such as less than about 5% by weight.

The product, diluted with an inert solvent such as heptane, if desired, is then sulfonated continuously or batchwise, preferably with SO$_3$ vapor, at between 15° and 75° C. in a molar ratio of about 1:1 SO$_3$ to naphthalene so as to attach an average of one SO$_3$H group to the naphthalene molecule. The degree of sulfonation can be monitored by analysis of the reaction mixture, such as by nonaqueous titration. It is not desirable to oversulfonate as the corrosion preventive properties of the final product are adversely affected. Thus, the sulfonation should be carefully controlled to provide an average of essentially one SO$_3$H group per naphthalene molecule. If desired, sulfuric acid or oleum can be used in place of SO$_3$ vapor, but they are not as effective, as unreacted sulfuric acid must be removed from the reaction mixture.

To recover the product, the sulfonation product can be diluted with heptane or other inert solvent and the mixture washed with an equal volume of water to remove any sulfuric acid and disulfonic acid derived from the alkylated naphthalene. The phases are separated and the organic phase is heated to 50°–90° C., preferably 65°–75° C., and the metal oxide, hydroxide, or carbonate, preferably in aqueous solution or suspension, is added in an amount to adjust the pH of the product to 6–12. Suitable metals include Mg, Ca, Ba, and Zn. The mixture is then allowed to cool to room temperature (30° C.) and the aqueous and organic phases are separated. The organic phase is then distilled to recover the solvent and obtain the metal sulfonate as a non-distillable residue.

To form a rust preventive, the sulfonate is preferably overbased. The term overbased is used to describe sulfonates which contain an amount of metal oxide or hydroxide in excess of that required to neutralize the sulfonic acid and which are carbonated to solubilize the excess metal oxide or hydroxide.

The following examples will serve to illustrate the invention and preferred embodiments. All parts and percentages in said examples and elsewhere in the specification and claims are by weight unless otherwise specified.

EXAMPLE 1

Two alkylation reactions were run in which a 10-gal. autoclave was charged with 13.0 lb. (0.10 lb.-mole) of Koppers HDS naphthalene, 7.11 lb. (0.05 lb.-mole) of Gulf Chemical Co. alpha-$C_{10}$ olefin (Gulftene-10), and 1.3 lb. of Filtrol 13LM activated clay. The autoclave was purged with nitrogen and then blanketed with 20 psig nitrogen while agitation and heating to 260° C. were begun. Upon reaching 260° C., an additional 21.34 lb. (0.15 lb.-mole) of alpha-$C_{10}$ olefin was charged via a metering pump over 60 minutes (120 minutes for the second reaction). The autoclave temperature was held at 260° C. during the addition. After the olefin addition was complete, the autoclave was maintained at 260° C. for three hours. At the end of the three hour period, the autoclave was cooled to 70° C. and the crude alkylate removed. The crude alkylate was then filtered in order to remove the clay catalyst.

Vacuum distillation of the crude alkylate was performed in two batches in a 22-liter stainless steel pot equipped with an 18-inch Vigreaux column. The crude alkylate was heated to a pot temperature of 275°–290° C. (vapor temperature of 215°–232° C.) at 6 torr in order to remove the mono-decylnaphthalene and unreacted olefin and naphthalene. The stripped material was then recombined, resulting in the following composition: 3.6 wt.% mono-decylnaphthalene; 49.5 wt.% di-decylnaphthalene; and 47 wt.% tri-decylnaphthalene. This composition has a corresponding calculated molecular weight of 454.

EXAMPLE 2

The alkylated product of Example 1 was diluted 1:1 by weight with heptane. The solution of alkylate in heptane was sprayed through the nozzle of a commercial, jet impact reactor (60 lb./hr.; 22° C.) into a gas stream containing $SO_3$ vapor (5.3 lb./hr.; 32° C.). The flow rates corresponded to a 1:1 molar ratio of $SO_3$ to alkylate. The hot acid produced was quenched with a recycle of ambient sulfonic acid, previously produced. Approximately one gallon (1,994 g.) of material was collected in 5.4 minutes.

Example 3

A 2-liter separatory funnel was charged with 580 g. (ca. 700 ml) of the sulfonic acid prepared in Example 2. The acid was shaken with ca. 720 ml of distilled water in order to remove a small amount of sulfuric acid. After the phases had separated, the lower, aqueous phase was removed and discarded. The organic phase was transferred to a 2-liter, 4-neck round-bottom flask equipped with a mechanical stirrer and thermometer. The flask and contents were heated to 70° C. and saturated, aqueous barium hydroxide solution, also at 70° C., was added portionwise until a pH of 12 was attained.

The contents of the flask were then transferred to a 2-liter separatory funnel to allow separation of the phases and to cool to room temperature. The lower, aqueous phase was withdrawn and discarded. The heptane solution of barium alkylnaphthalenesulfonate (633 g) was transferred to a distilling flask equipped for vacuum distillation. The heptane was stripped to a pot temperature of about 130° C. at 21 torr. Analysis of the pot residue gave the following results: sulfonate value calculated as acid number, 65.5; weight percent barium, 9.2; weight percent sulfur, 4.7; and weight percent water, 1.0.

EXAMPLE 4

The following example illustrates the preparation of a rust preventive of the invention.

| EXAMPLE | |
|---|---|
| Ingredients | Amounts |
| HVT 200 Neutral MQ (Mineral Oil SAE 10) | 0.77 gal. |
| Kraton 1657 OS, an ethylene-butene co-polymer manufactured by Shell Chemical Co. | 2.81 lb. |
| ARCO PEW-1, a high Mol Wt polyethylene manufactured by Atlantic Richfield Co. | 4.25 lb. |
| Benton-type grease | 10.82 lb. |
| Plasticrude NX, a wax manufactured by Texaco, Inc. | 38.49 lb. |
| Lampblack, RAVEN 22, a carbon black manufactured by City Services Co. | 1.02 lb. |
| Ex. 3, a composition of the invention | 12.78 lb. |
| U.O.P. 688, an oxidation inhibitor manufactured by Universal Oil Products | 0.9 lb |

The above ingredients were mixed at room temperature in a kettle and the mixture was heated to 143°–149° C. to dissolve the Kraton and ARCO polymers. Then, $CO_2$ (98 lb.) was bubbled into the mixture while adding 21.88 lb. of hydrated lime at 110°–121° C. to overbase the sulfonate. Tall oil pitch (0.28 gal.) was then added to the mixture at room temperature.

The composition was tested as a thermoplastic corrosion preventive compound for application on sheet metal components. It was applied over hot (105°–120° C.), clean, bare steel in a hot dip system (105°–120° C.) to a firmly adhering, low gloss film 75 μm to 125 μm (3 to 5 mils) thick. The coating was 100% solids with no solvents. It did not contain asphalt or fibrous fillers such as asbestos. It is non-toxic and non-injurious to plant personnel.

Each of three panels was subjected to a different test: (1) 1,000 hour salt spray; (2) gravel test followed by a 336 hour salt spray; and (3) 100 hour QUV followed by a 336 hour salt spray. At a 6% concentration of barium didecylnaphthalenesulfonate, the panels did not exhibit evidence of corrosion. A 12.8% concentration of barium di-nonylnaphthalenesulfonate (King Industries' BSN) was required to obtain comparable results to the composition of the invention. Moreover, the novel compound provided additional protection such that the metal did not rust when the coating was damaged, and in some areas where the coating became scratched or nicked, the exposed metal did not exhibit corrosion effects even after an additional 400 hours of salt spray.

What is claimed is:

1. Rust preventive water insoluble compounds of the formula

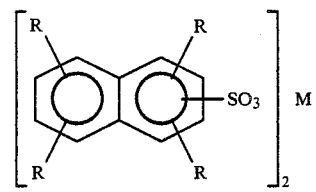

wherein the R groups are independently selected from methyl, hydrogen, and decyl of the formula

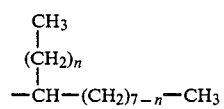

wherein n=0 to 3; and wherein from two to three R groups are decyl, zero to two R groups are methyl, and zero to two R groups are hydrogen; and M is a divalent metal selected from Mg, Ca, Ba, and Zn.

2. The compound of claim 1 wherein M is Ba.

3. The compound of claim 1 wherein two R groups are decyl.

4. The compound of claim 1 wherein three R groups are decyl.

5. The compound of claim 1 wherein n=0.

6. A mixture of compounds of claim 1 wherein one compound has two R groups which are decyl and another has three R groups which are decyl.

7. A mixture of compounds of claim 1 comprising: (1) a compound wherein two R groups are decyl and two are hydrogen, (2) a compound wherein three R groups are decyl and one is hydrogen, and (3) a minor amount of less than 5% of a compound wherein one R group is decyl and three R groups are hydrogen; and M is barium in each of said compounds.

8. The mixture of claim 7 wherein n=0.

9. The compound of claim 1 wherein it is overbased.

10. A rust preventive consisting essentially of a compound of claim 9.

11. Rust preventive water insoluble compounds of the formula

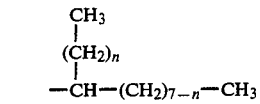

wherein the R groups are independently selected from methyl, hydrogen, and decyl of the formula $$\begin{array}{c} CH_3 \\ | \\ (CH_2)_n \\ | \\ -CH-(CH_2)_{7-n}-CH_3 \end{array}$$

wherein n=0 to 3; and wherein from two to three R groups are decyl, zero to two R groups are methyl, and zero to two R groups are hydrogen.

12. The compound of claim 11 wherein two R groups are decyl.

13. The compound of claim 11 wherein three R groups are decyl.

14. The compound of claim 11 wherein n=0.

15. A mixture of compounds of claim 11 wherein one compound has two decyl R groups and another has three decyl R groups.

16. A mixture of compounds of claim 11 comprising: (1) a compound wherein two R groups are decyl and two are hydrogen, (2) a compound wherein three R groups are decyl and one is hydrogen, and (3) a minor amount of less than 5% of a compound wherein one R group is decyl and three R groups are hydrogen.

* * * * *